US012357019B2

(12) United States Patent
Mishra et al.

(10) Patent No.: US 12,357,019 B2
(45) Date of Patent: Jul. 15, 2025

(54) SOFT ORAL PRODUCT

(71) Applicant: Altria Client Services LLC, Richmond, VA (US)

(72) Inventors: Munmaya K. Mishra, Manakin Sabot, VA (US); Georgios D. Karles, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 28 days.

(21) Appl. No.: 18/452,662

(22) Filed: Aug. 21, 2023

(65) Prior Publication Data

US 2023/0389596 A1 Dec. 7, 2023

Related U.S. Application Data

(60) Continuation of application No. 17/075,026, filed on Oct. 20, 2020, now Pat. No. 11,758,938, which is a
(Continued)

(51) Int. Cl.
*A24B 15/28* (2006.01)
*A24B 13/00* (2006.01)
*A24B 15/30* (2006.01)
*A24B 15/36* (2006.01)
*A61K 9/00* (2006.01)
(Continued)

(52) U.S. Cl.
CPC ............ *A24B 15/283* (2013.01); *A24B 13/00* (2013.01); *A24B 15/301* (2013.01); *A24B 15/302* (2013.01); *A24B 15/303* (2013.01); *A24B 15/308* (2013.01); *A24B 15/365* (2013.01); *A61K 9/0056* (2013.01);
(Continued)

(58) Field of Classification Search
None
See application file for complete search history.

(56) References Cited

U.S. PATENT DOCUMENTS 2,162,738 A 6/1939 McCoy
3,139,436 A 6/1964 Bicking
(Continued)

FOREIGN PATENT DOCUMENTS

GB 1176667 A 1/1970
WO WO-2006/000232 A1 1/2006
WO WO-2008/002691 A2 1/2008

OTHER PUBLICATIONS

Definition of "matrix". The Free Dictionary, no date, [online], retrieved from the Internet, [retrieved Oct. 11, 2017], <URL: http://www.thefreedictionary.com/matrix>. (Year: 2017).*
(Continued)

*Primary Examiner* — Dennis R Cordray
(74) *Attorney, Agent, or Firm* — Harness, Dickey & Pierce, P.L.C.

(57) ABSTRACT

An oral product includes a body that is wholly receivable in an oral cavity. The body includes a polymer matrix and one or more flavorants and/or active ingredients embedded in the polymer matrix. The polymer matrix can include a copolymer of ethylene and one or more vinyl monomers or zein. For example, the polymer can be ethylene-vinyl acetate copolymer and/or ethylene-vinyl alcohol copolymer. In some cases, the oral product can include tobacco and/or nicotine.

20 Claims, 9 Drawing Sheets

Related U.S. Application Data continuation of application No. 16/371,219, filed on Apr. 1, 2019, now Pat. No. 10,834,960, which is a continuation of application No. 15/220,604, filed on Jul. 27, 2016, now Pat. No. 10,244,787, which is a division of application No. 14/206,541, filed on Mar. 12, 2014, now Pat. No. 9,420,827.

(60) Provisional application No. 61/786,195, filed on Mar. 14, 2013.

(51) Int. Cl.
  *A61K 9/68* (2006.01)
  *A61K 47/32* (2006.01)
  *A61K 47/42* (2017.01)

(52) U.S. Cl.
  CPC ............ *A61K 9/0058* (2013.01); *A61K 47/32* (2013.01); *A61K 47/42* (2013.01)

(56) References Cited

U.S. PATENT DOCUMENTS

| | | | |
|---|---|---|---|
| 3,396,735 | A | 8/1968 | Von Bethmann et al. |
| 4,153,063 | A | 5/1979 | Roselius et al. |
| 4,448,208 | A | 5/1984 | Friedrich et al. |
| 4,515,769 | A | 5/1985 | Merritt et al. |
| 4,516,590 | A | 5/1985 | Teng |
| 4,528,993 | A | 7/1985 | Sensabaugh, Jr. et al. |
| 4,660,577 | A | 4/1987 | Sensabaugh et al. |
| 4,848,373 | A | 7/1989 | Lenkey |
| 4,987,907 | A | 1/1991 | Townend |
| 5,372,149 | A | 12/1994 | Roth et al. |
| 5,487,792 | A | 1/1996 | King et al. |
| 5,545,414 | A | 8/1996 | Behr et al. |
| 6,010,720 | A | 1/2000 | Derrieu et al. |
| 6,344,222 | B1 | 2/2002 | Cherukuri et al. |
| 6,596,298 | B2 | 7/2003 | Leung et al. |
| 6,613,833 | B2 | 9/2003 | Kawahara et al. |
| 7,524,895 | B2 | 4/2009 | Ikeda et al. |
| 9,420,827 | B2 * | 8/2016 | Mishra ................. A24B 15/303 |
| 10,244,787 | B2 * | 4/2019 | Mishra ................... A61K 47/42 |
| 10,834,960 | B2 * | 11/2020 | Mishra ................. A24B 15/302 |
| 2003/0049318 | A1 | 3/2003 | Davis et al. |
| 2003/0206942 | A1 | 11/2003 | Kulkarni et al. |
| 2003/0211136 | A1 * | 11/2003 | Kulkarni ................... A61K 8/60 514/420 |
| 2004/0052851 | A1 | 3/2004 | Graff et al. |
| 2004/0118422 | A1 | 6/2004 | Lundin et al. |
| 2005/0178398 | A1 | 8/2005 | Breslin et al. |
| 2006/0198873 | A1 | 9/2006 | Chan et al. |
| 2008/0187621 | A1 | 8/2008 | Boghani et al. |
| 2008/0209586 | A1 | 8/2008 | Nielsen et al. |
| 2008/0286340 | A1 * | 11/2008 | Andersson ............... A23G 4/14 424/440 |
| 2009/0025739 | A1 | 1/2009 | Brinkley et al. |
| 2009/0095313 | A1 | 4/2009 | Fuisz |
| 2009/0098192 | A1 | 4/2009 | Fuisz |
| 2009/0196834 | A1 | 8/2009 | Andersen |
| 2010/0255064 | A1 | 10/2010 | Andersen et al. |
| 2010/0266669 | A1 | 10/2010 | Meyer et al. |
| 2010/0282267 | A1 | 11/2010 | Atchley |
| 2010/0291245 | A1 | 11/2010 | Gao et al. |
| 2010/0326454 | A1 | 12/2010 | Fuisz |
| 2011/0083688 | A1 | 4/2011 | Mishra et al. |
| 2011/0108043 | A1 | 5/2011 | Ettireddy et al. |
| 2012/0318287 | A1 | 12/2012 | Andersen |
| 2013/0186417 | A1 | 7/2013 | Gao et al. |

OTHER PUBLICATIONS

International Preliminary Report on Patentability in International Application No. PCT/US2014/024683, mailed Sep. 24, 2015, 14 pages.
Japanese Office Action in Application No. 2016-501603, dated Nov. 8, 2017, 9 pages.
Takahashi, et al. "Crystal Structure of Ethylene-Vinyl Alcohol Copolymers," Macromolecules, 32, pp. 5860-5871 (1999).
Tso, "Chapter 1:Seed to Smoke," Tobacco, Production, Chemistry and Technology, Davis & Nielsen, Eds. 1999, 33 pages.
International Search Report and Written Opinion for Application No. PCT/US2014/024683 dated Oct. 14, 2014.
International Preliminary Report and Written Opinion for corresponding Application No. PCT/US2014/024683 dated Sep. 15, 2015.
Definition of "matrix", The Free Dictionary, no date, [online], retrieved from the Internet, Oct. 11, 2017, <URL:http://www.thefreedictionary.com/matrix>.
Japanese Notice of Reasons for Rejection for corresponding Application No. 2018-173226, dated Nov. 18, 2019, English translation thereof.
Non-Final Office Action issued Aug. 11, 2015 in U.S. Appl. No. 14/206,541.
Non-Final Office Action issued Nov. 24, 2015 in U.S. Appl. No. 14/206,541.
Notice of Allowance issued Apr. 27, 2016 in U.S. Appl. No. 14/206,541.
Non-Final Office Action issued Feb. 21, 2018 in U.S. Appl. No. 15/220,604.
Final Office Action issued Aug. 2, 2018 in U.S. Appl. No. 15/220,604.
Notice of Allowance issued Dec. 3, 2018 in U.S. Appl. No. 15/220,604.
Non-Final Office Action issued Apr. 8, 2020 in U.S. Appl. No. 16/371,219.
Notice of Allowance issued Jul. 23, 2020 in U.S. Appl. No. 16/371,219.
Kamath etal,"Crystallinity of ethylene-vinyl acetate copolymers" J. Applied Science, V9, pp. 3153-3160, 1965, [online] retrieved from the Internet, [retrieved Jan. 9, 2023], <https://onlinelibrary.wiley.com/doi/epdf/10.1002/app.1965.070090919> (Year: 1965).

* cited by examiner

110A

110B

110C

110D

110E

110F

SOFT ORAL PRODUCT

CROSS REFERENCE TO RELATED APPLICATIONS

This application is a Continuation application of U.S. application Ser. No. 17/075,026, filed Oct. 20, 2020, which is a Continuation application of U.S. application Ser. No. 16/371,219, filed Apr. 1, 2019, which is a Continuation application of U.S. application Ser. No. 15/220,604, filed Jul. 27, 2016, which is a Divisional application of, and claims the benefit of priority under U.S.C. § 121 to, U.S. application Ser. No. 14/206,541 filed Mar. 12, 2014, which claims the benefit of priority under 35 U.S.C. § 119(e) to U.S. Application No. 61/786,195 filed Mar. 14, 2013, the entire contents of each of which are incorporated herein by reference.

TECHNICAL FIELD

This document relates to soft oral products including certain polymers and one or more flavors and/or active ingredients. In some case, the polymer can be ethylene vinyl acetate copolymer, ethylene vinyl alcohol copolymer, zein, gelatin, or a combination thereof. In some cases, the soft oral product can include tobacco.

BACKGROUND

Tobacco compositions are available to adult tobacco consumers in a variety of forms. Smoking tobacco is combusted and the aerosol either tasted or inhaled (e.g., in a cigarette, cigar, or pipe). Smokeless tobacco products are not combusted and include: chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between a cheek and gum of an adult tobacco consumer. Snus is a heat treated smokeless tobacco. Dry snuff is finely ground tobacco that is placed in the mouth or used nasally.

SUMMARY

This document describes an oral product that provides a satisfying tactile and/or flavor experience. The oral product includes a body that is at least partially receivable in an oral cavity of an adult consumer. In some cases, the body includes a polymer matrix of a copolymer of ethylene and a vinyl monomer. In some cases, the body includes a matrix of zein. In some cases, the body includes a matrix of gelatin. In some cases, the body includes a matrix including a combination of a copolymer, zein, and/or gelatin. In some cases, the matrix can include one or more flavors and/or active ingredients. For example, the matrix can include tobacco.

The oral products provided herein can optionally include one or more of the following features. In some cases, the body of the oral product includes at least 10 weight percent of the copolymer, the zein, and/or the gelatin. The copolymer can be a random copolymer. In some cases, the copolymer can be a block copolymer. In some cases, the copolymer can include ethylene and vinyl acetate. In some cases, the copolymer can include ethylene and vinyl alcohol. In some cases, the copolymer includes between 25 percent by weight and 40 percent by weight vinyl monomers. The oral product provided herein can include a plasticizer and/or a surfactant dispersed in the mouth-stable polymer matrix. For example, the plasticizer can be propylene glycol, glycerin, vegetable oil, triglycerides, or a combination thereof. The oral product can also include a sweetener dispersed in the body. The sweetener can be saccharine, sucralose, aspartame, acesulfame potassium, or a combination thereof.

The oral product, according to certain embodiments, includes one or more additives. For example, the oral product can include an additive selected from the group consisting of minerals, vitamins, dietary supplements, nutraceuticals, energizing agents, soothing agents, amino acids, chemesthesis agents, antioxidants, botanicals, teeth whitening agents, therapeutic agents, or a combination thereof.

The body of the oral product can have at least 10 weight percent celluloid fibers. In some cases, the celluloid fibers can include tobacco fibers. In some cases, the oral product can include non-tobacco celluloid fibers. For example, the celluloid fibers can be selected from the following: sugar beet fiber, wood pulp fiber, cotton fiber, bran fiber, citrus pulp fiber, grass fiber, willow fiber, poplar fiber, and combinations thereof. The non-tobacco celluloid fibers may also be chemically treated prior to use. For example, the non-tobacco celluloid fibers can be CMC, HPMC, HPC, or other treated cellulosic material.

The oral product can include flavorants. The flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamon, apium graveolens, clove, cascarilla, nutmeg, sandalwood, bergamot, geranium, honey essence, rose oil, vanilla, lemon oil, orange oil, Japanese mint, cassia, caraway, cognac, jasmine, chamomile, menthol, ylang-ylang, sage, fennel, piment, ginger, anise, coriander, coffee, mint oils from a species of the genus Mentha, cocoa, and combinations thereof. Synthetic flavorants can also be used. The particular combination of flavorants can be selected from the flavorants that are generally recognized as safe ("GRAS") in a particular country, such as the United States. Flavorants can also be included in the oral product as encapsulated flavorants.

The body of the oral product can have a variety of different shapes, some of which include disk, shield, rectangle, and square. According to certain embodiments, the body can have a length or width of between 5 mm and 25 mm and a thickness of between 1 mm and 10 mm.

The body of the oral product can be compressible and springy. In some cases, the body can return to an original shape after being deformed by an adult consumer using a chewing action. As the oral product is worked to release flavors and/or active ingredients, the oral product can become flatter, yet still retain some shape memory, unlike a chewing gum. In some cases, the oral product can have chewing gum-like chewing properties, yet not be sticky.

In general, another aspect of the subject matter described in this specification is methods of making and using the oral product. The methods of making the oral product can include the actions of extruding a mouth-stable polymer having tobacco fibers dispersed therein.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
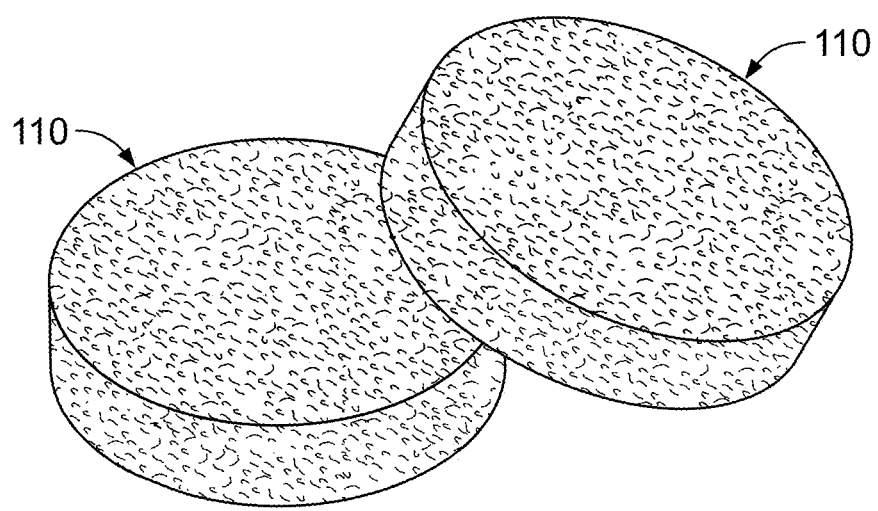
FIG. 1 is a perspective view of a pair of oral products.

The oral products described herein include a polymer matrix and one or more flavorants and/or active ingredients embedded therein. The polymer matrix can include a copolymer of ethylene and a vinyl monomer (e.g., ethylene-vinyl acetate or ethylene-vinyl alcohol). In some cases, the polymer matrix can include zein. In some cases, the polymer matrix can include gelatin. In some cases, the oral products described herein can include tobacco and can provide a favorable tobacco experience.

The oral product can include ethylene-vinyl acetate copolymer. Ethylene-vinyl acetate copolymer can have properties that approach the properties of elastomeric materials in softness and flexibility, yet can be processed like other thermoplastics. In some cases, the ethylene-vinyl acetate copolymer can be a random copolymer. In some cases, the ethylene-vinyl acetate copolymer can include between 25% by weight and 40% by weight of vinyl acetate. A higher percentage of vinyl acetate can increase the softness of the ethylene-vinyl acetate copolymer. In some cases, the ethylene-vinyl acetate copolymer is amorphous. In some cases, the oral product can include nicotine. Nicotine can bind to the vinyl acetate groups and held slow a release of nicotine into a mouth of an adult consumer during use. The ethylene-vinyl acetate copolymer can be shaped (e.g., extruded) at a temperature of about 100° C., thus it can be mixed and shaped with flavorants and/or active ingredients that might volatize or degrade if heated to higher temperatures.

The oral product can include ethylene-vinyl alcohol copolymer. Ethylene-vinyl alcohol copolymer can be prepared by polymerization of ethylene and vinyl acetate to give the ethylene-vinyl acetate copolymer followed by hydrolysis to convert the vinyl acetate units into vinyl alcohol units. In some cases, the ethylene-vinyl alcohol copolymer can be a random copolymer. In some cases, the ethylene-vinyl alcohol copolymer can include between 25% by weight and 40% by weight of vinyl alcohol. In some cases, the ethylene-vinyl acetate copolymer is amorphous. The ethylene-vinyl alcohol copolymer can be shaped (e.g., extruded) at a temperature of 100° C. or less, thus it can be mixed and shaped with flavorants and/or active ingredients that might volatize or degrade if heated to higher temperatures. In some cases, the polymer can include a mixture of ethylene-vinyl alcohol copolymer and ethylene-vinyl acetate copolymer.

In some cases, the oral product can include zein as a matrix for holding tobacco. Zein is a class of prolamine protein. In some cases, the zein can be corn zein, which is found in maize. Zein is clear, odorless, tasteless, water-insoluble, and edible.

In some cases, the oral product can include gelatin as a matrix for holding tobacco. Gelatin is a mixture of peptides and proteins produced by partial hydrolysis of collagen extracted from, for example, the skin, boiled crushed horn, hoof and bones, connective tissues, organs and some intestines of animals such as domesticated cattle, chicken, pigs, and horses. The natural molecular bonds between individual collagen strands are broken down into a form that rearranges more easily. Gelatin melts to a liquid when heated and solidifies when cooled again. Together with water, it can form a semi-solid colloid gel.

The polymer matrix can be mouth stable. As used here, the term "mouth stable" means that the polymer does not appreciably dissolve or disintegrate when exposed to saliva within an oral cavity and at the normal human body temperature (e.g., about 98.6° F.) over a period of one hour. In some cases, the oral products described herein can remain intact when placed within an oral cavity during a use period. After use, the mouth-stable polymer matrix can be removed from the oral cavity and discarded.

One or more additives are included in the oral product and adapted to be released from the oral product when the oral product is placed in an oral cavity. The oral product, in some cases, includes added nicotine and/or other additives. Celluloid fibers can help to provide access to nicotine and/or other additives throughout the oral product. During use, saliva can be absorbed into the polymer matrix to release the nicotine and/or other additives. In some cases, the oral product can include tobacco (e.g., tobacco fibers). The absorbed saliva can cause the celluloid fibers (e.g., tobacco fibers and/or non-tobacco fibers) to expand, which can facilitate further release of tobacco constituents, additives, sweeteners, and/or flavorants. Mechanical action (e.g., chewing) of the oral product can facilitate the release of the additives, sweeteners, and/or flavorants.

In addition to additives, sweeteners, and flavorants, the oral product can also include fillers, plasticizers, and/or processing aids. Fillers can also be included in the polymer matrix to alter the texture or pliability of the oral product. For example, starch deposits can be included and designed to be crushed during the chewing of the oral product. The polymer matrix can also include surfactants and/or plasticizers, which can increase the softness of the oral product. Processing aids can also be present in the oral product and be used to facilitate shaping processes.

Oral Product Shapes and Packaging

FIG. 1 depicts an example of an oral product 110. The oral product 110 has a disk shape. For example, the oral product 110 can have a diameter of about 12 mm and a thickness of about 2.5 mm.

Figure 2A:
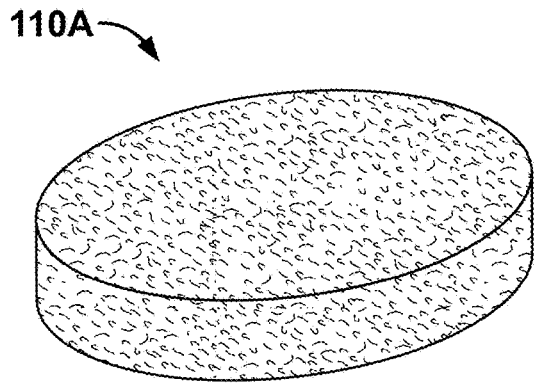
FIGS. 2A-2O illustrate various exemplary shapes of oral products.
Figure 2B:
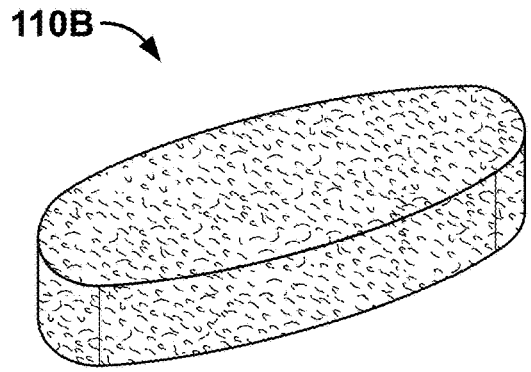
Figure 2C:
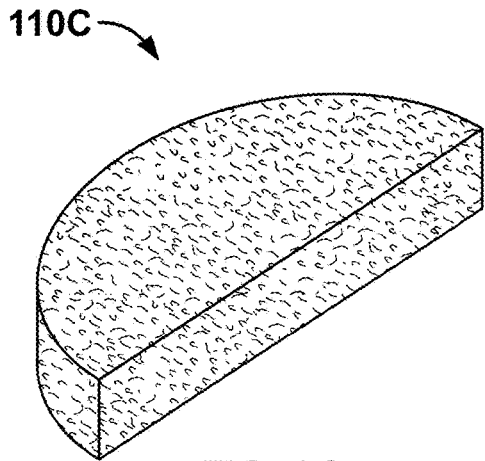
Figure 2D:
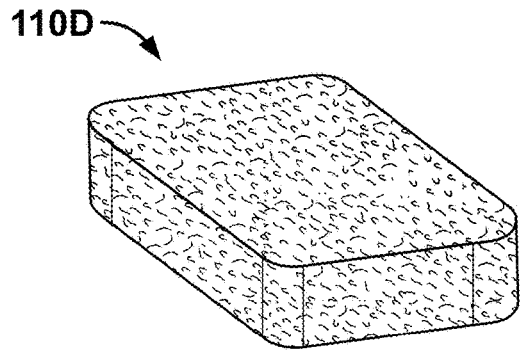
Figure 2E:
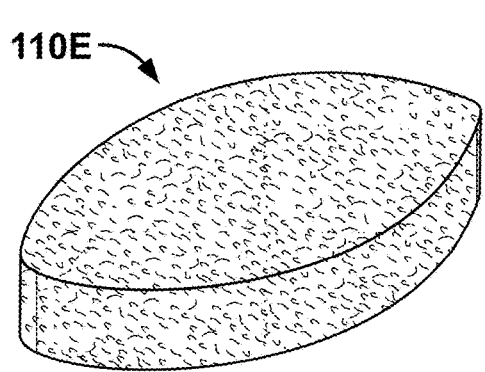
Figure 2F:
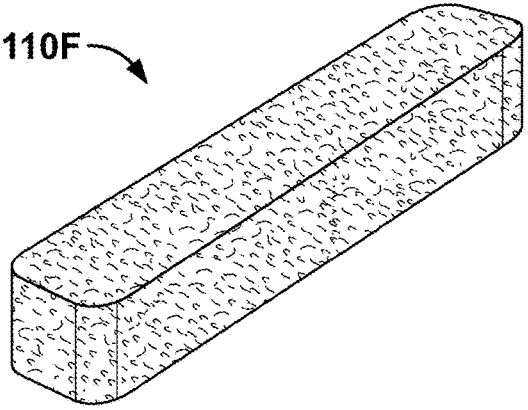
Figure 2G:
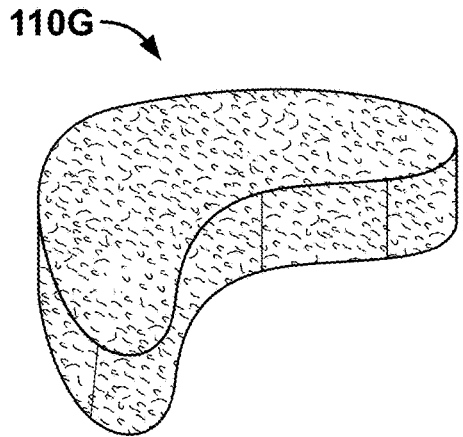
Figure 2H:
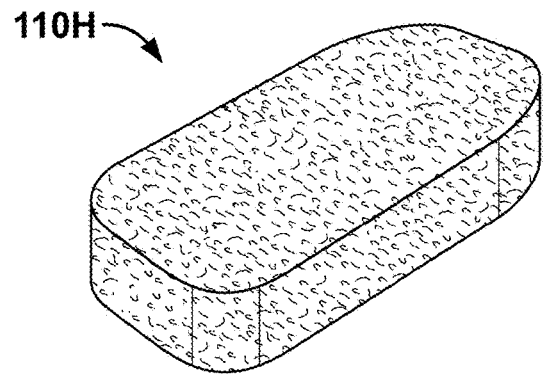
Figure 2I:
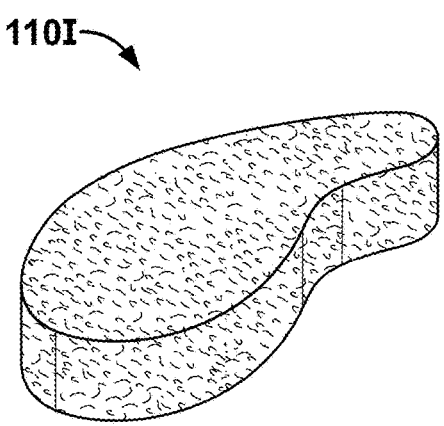
Figure 2J:
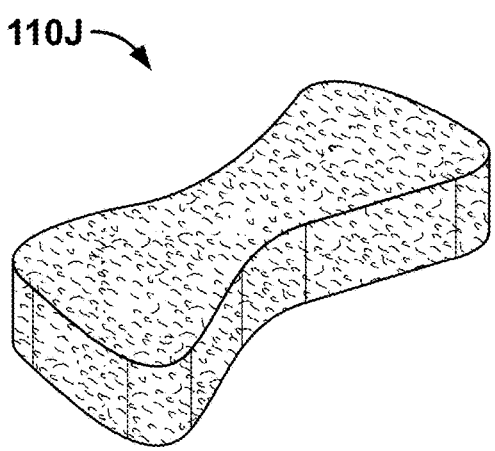
Figure 2K:
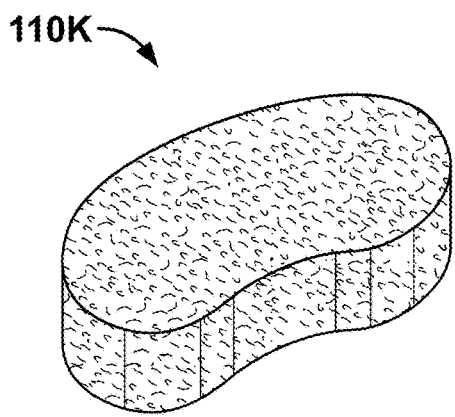
Figure 2L:
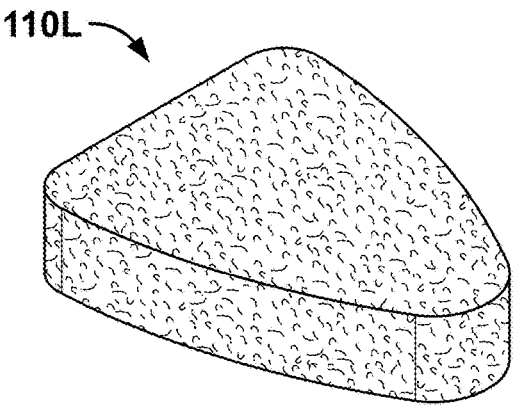
Figure 2M:
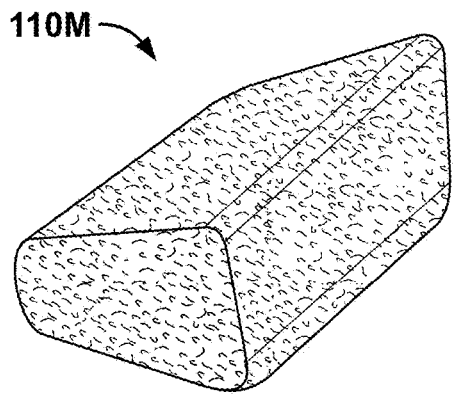
Figure 2N:
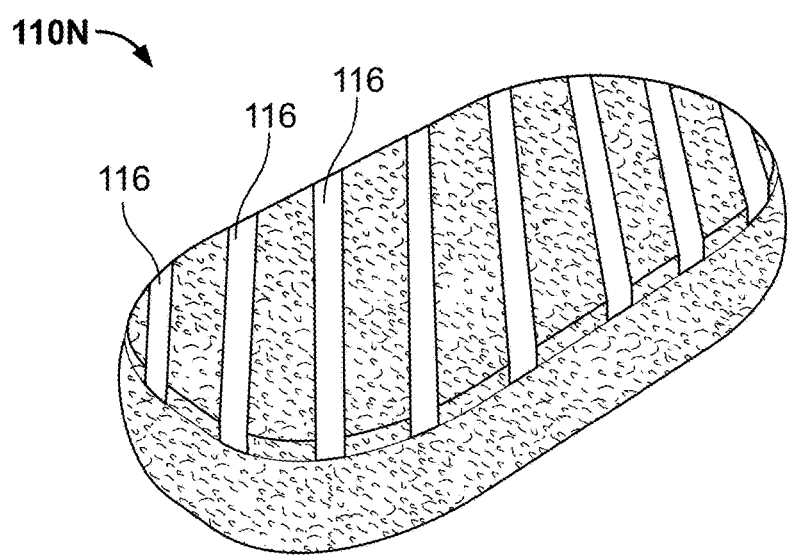

Referring now to FIGS. 2A-2N, the oral product 110 can be molded into any desired shape. For example, referring to FIGS. 2A-2L, the oral product 110A-L can be formed in a shape that promotes improved oral positioning in the oral cavity, improved packaging characteristics, or both. In some circumstances, the oral product 110A-L can be configured to be: (A) an elliptical-shaped oral product 110A; (B) an elongated elliptical-shaped oral product 110B; (C) semicircular oral product 110C; (D) square or rectangular-shaped oral product 110D; (E) football-shaped oral product 110E; (F) elongated rectangular-shaped oral product 110F; (G) boomerang-shaped oral product 110G; (H) rounded-edge rectangular-shaped oral product 110H; (I) teardrop- or comma-shaped oral product 110I; (J) bowtie-shaped oral product 110J; (K) peanut-shaped oral product 110K; and (L) shield-shaped oral product. Alternatively, the oral product can have different thicknesses or dimensionality, such that a beveled article (e.g., a wedge) is produced (see, for example, product 110M depicted in FIG. 2M) or a hemi-spherical shape is produced. In some cases, the oral product has a shield shape.

In addition or in the alternative to flavorants being included within the mouth-stable polymer matrix, flavorants can be included on an exterior of the oral product 110. For example, referring to FIG. 2N, for example, some embodiments of an oral product 110N can be equipped with flavor strips 116.

Figure 2O:
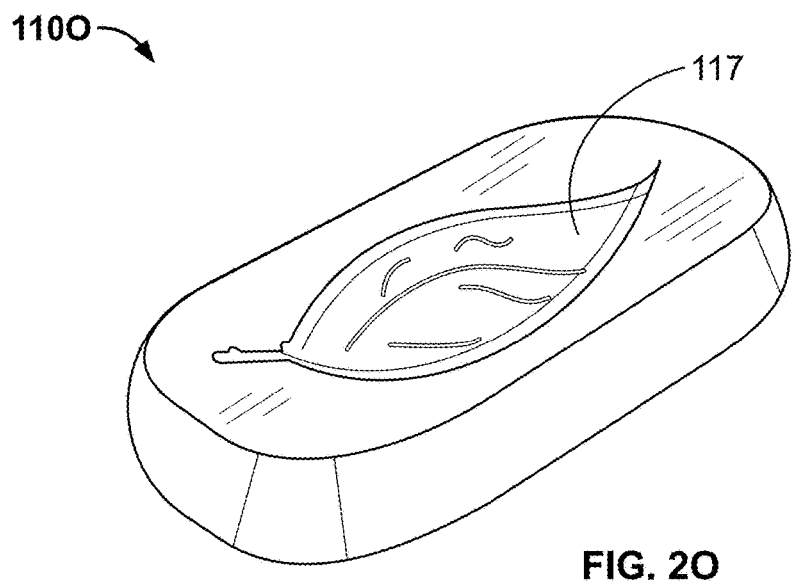

Referring to FIG. 2O, particular embodiments of the oral product 110 can be embossed or stamped with a design (e.g., a logo, an image, or the like). For example, the oral product 110O can be embossed or stamped with any type of design 117 including, but not limited to, a trademark, a product name, or any type of image. The design 117 can be formed directly into the oral product, arranged along the exterior of the product 110O. The design 117 can also be embossed or stamped into those embodiments with a dissolvable film 116 applied thereto.

In some cases, the oral product 110 or products 110A-0 can be wrapped or coated in an edible or dissolvable film, which may be substantially transparent or translucent. The dissolvable film can readily dissipate when the oral product 110 is placed in an oral cavity.

One or more oral products 110 can be packaged in a variety of conventional and non-conventional manners. For example, a plurality of oral products 110 can be packaged in a container having a lid. In other embodiments, a plurality of oral products 110 can be stacked and packaged in a paper, plastic, and/or aluminum foil tube. The packaging can have a child-resistant lid.

Figure 3A:
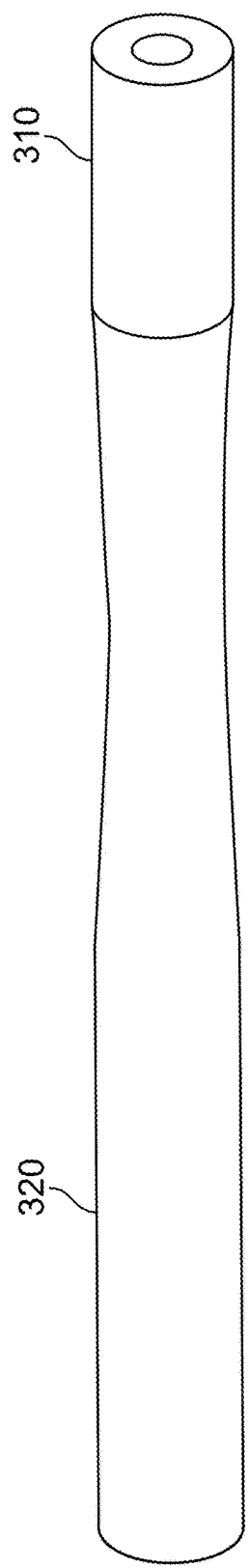
FIG. 3A-3J illustrate oral products having various rod, stick, or tube configurations.
Figure 3B:
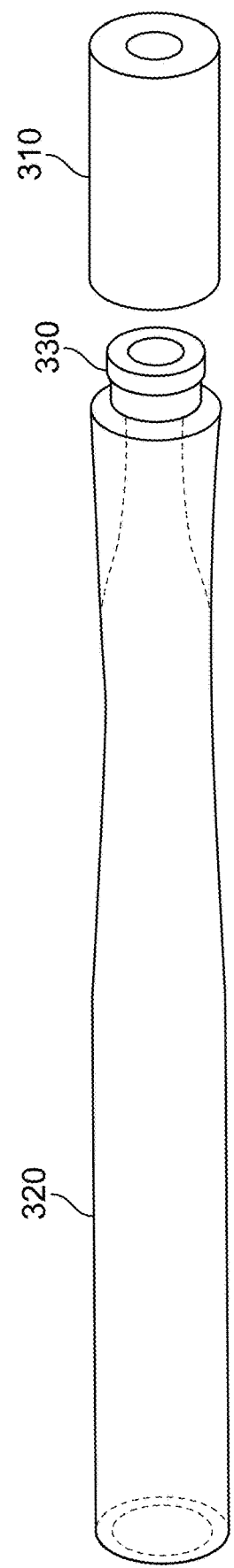

The oral product 110 can also include additional elements. In some cases, a polymer matrix including one or more flavorants and/or active ingredients (e.g., tobacco fibers) can be attached to a rod, tube, or stick. For example, FIGS. 3A-3J illustrate tubes attached to a polymer matrix tips. FIG. 3A depicts an embodiment of an oral product having a tip piece 310 and a tube piece 320. In some cases, the tip piece 310 can include the polymer matrix (e.g., ethylene-vinyl acetate copolymer) and tobacco within the polymer matrix. In some cases, the tip piece 310 can include the polymer matrix (e.g., ethylene-vinyl acetate copolymer) and nicotine. The tip piece 310 can be sized and shaped to be at least partially received in an oral cavity. The tube piece 320 can be made of any conventional polymer. During use the tube piece 320 can act as holder for the tip piece 310. The tube piece 320 and the tip piece 310 can be attached by a snap-fit attachment feature 330, as shown in FIG. 3B.

Figure 3C:
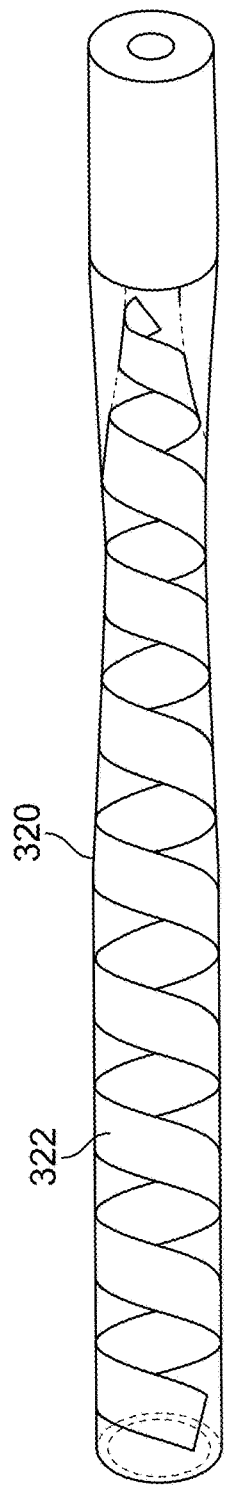
Figure 3D:
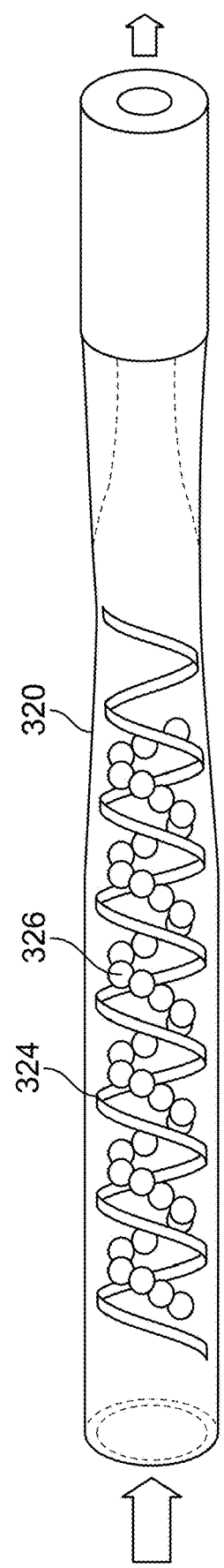
Figure 3E:
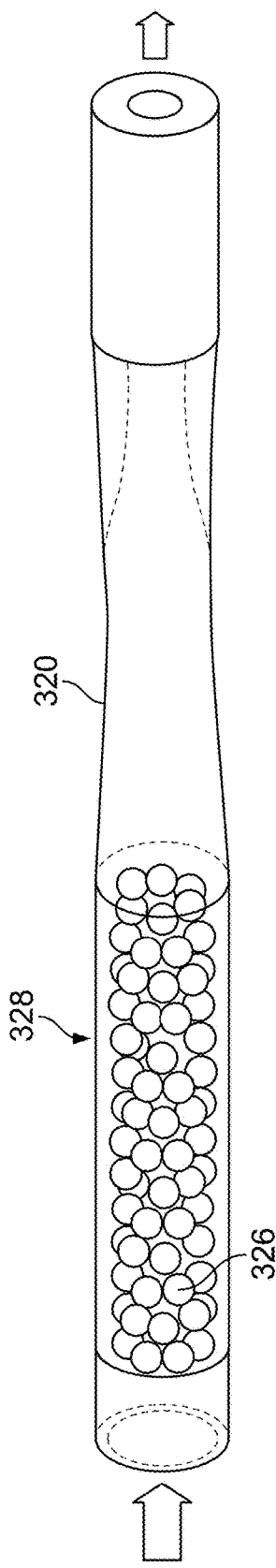
Figure 3F:
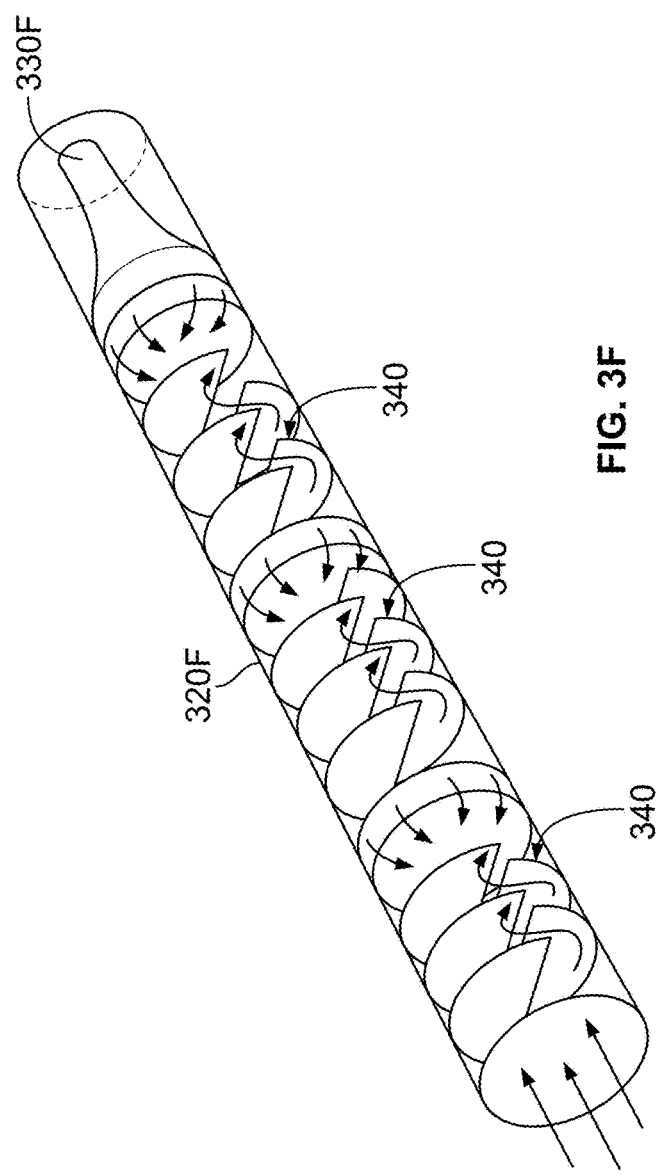

The tube piece 320 can be reusable. For example, multiple tip pieces 310 can be packaged with a single tube piece 320 and a user can switch off the tip pieces 310. In some cases, the tube pieces 320 can be intended for a single use. In some cases, the tube pieces 320 can include flavorants within the tube. The flavorants can be adapted to be released when air is drawn through the tube 320. For example, FIG. 3C depicts a tube including a flavor ribbon 322. FIG. 3D depicts a tube 320 including a flavor strip 324 and a plurality of flavor beads 326. FIG. 3E depicts a tube 320 including a compressed mass 328 of flavor beads 326. In some cases, the inside of the tube can have structure adapted to alter the flow pattern of air drawn into the tube. For example, FIG. 3F depicts a tube 320F having a series of steps and constrictions 340 adapted to alter the flow pattern of air drawn into the tube. FIG. 3F also depicts an alternative connection feature 330F.

Figure 3G:
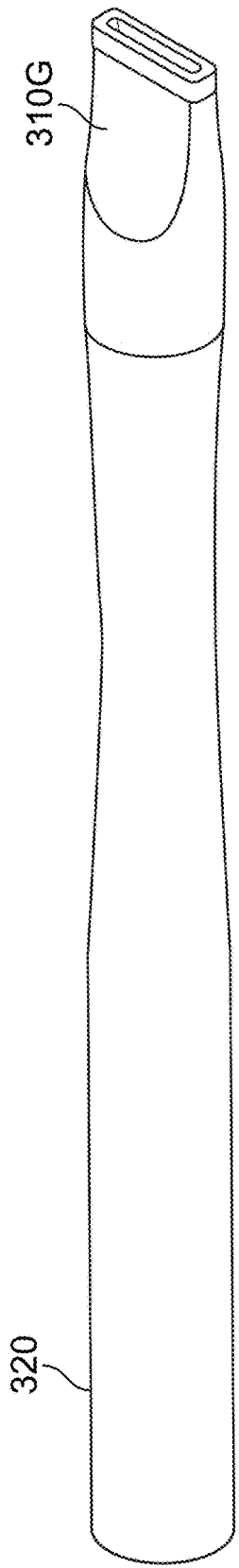

FIG. 3G depicts an embodiment having a recorder-like shape. As shown, a tip piece 310G is connected to the contoured tube piece 320. For example, the recorder-shaped tip 310G can be composed of a mouth-stable polymer matrix that includes tobacco fibers, one or more sweeteners, and one or more flavorants. As shown, the tip piece 310G is sized and shaped to be at least partially received within an oral cavity of an adult tobacco consumer.

Figure 3H:
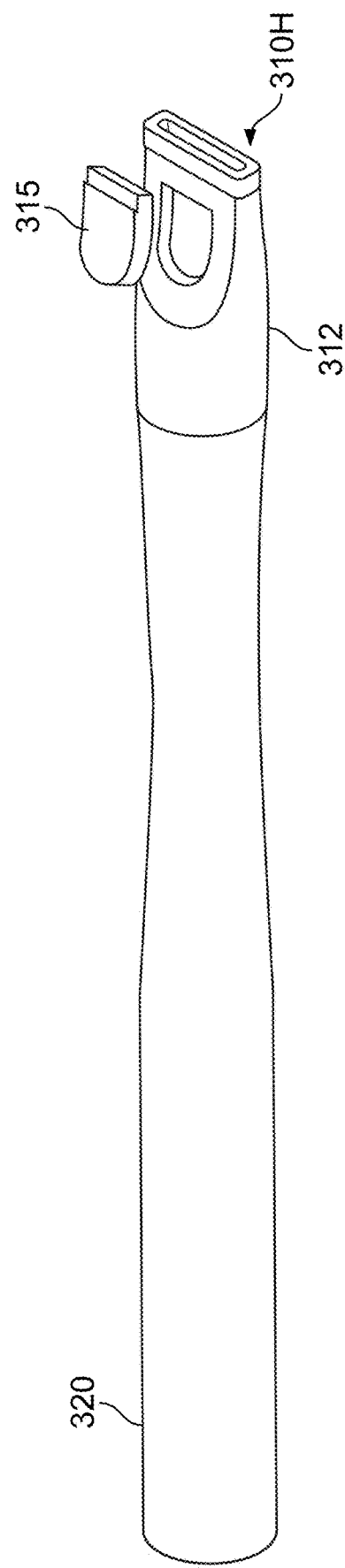
Figure 3I:
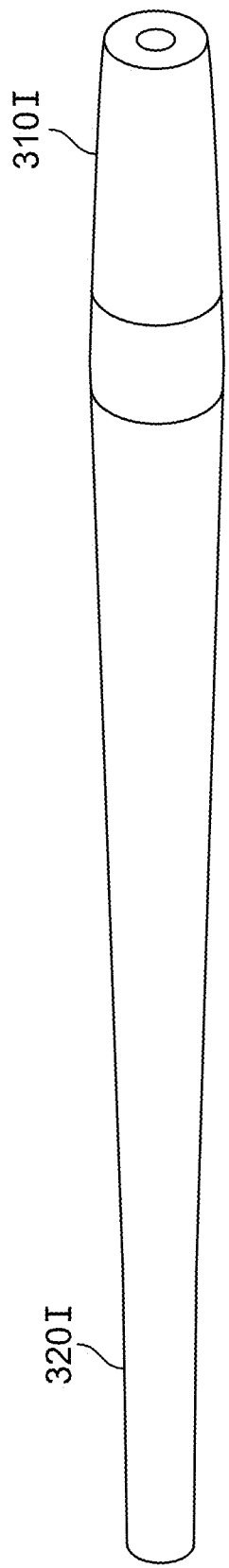
Figure 3J:
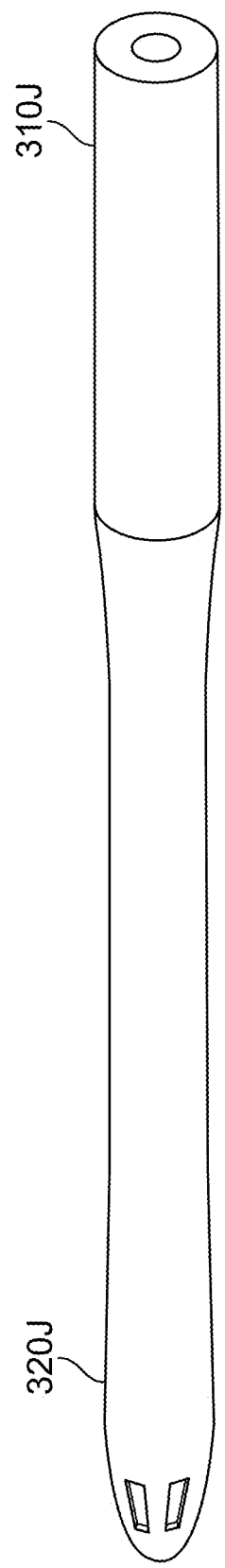

FIG. 3H depicts a similarly shaped oral product having a plastic recorder-shaped tip 310H that includes a reusable plastic part 312 and a mouth-stable polymer matrix part 315 having tobacco fibers dispersed therein. FIGS. 3I and 3J depict embodiments having alternatively shaped tip pieces 310I and 310J. FIG. 3I depicts an embodiment having a tapered tube 320I. FIG. 3J depicts an embodiment having vent holes at the non-tip end of the tube piece 320J.

In some cases, a system or kit of different tubes and rods and/or different tips can be packaged together, each having the same type of attachment features. Embodiments having each of the combinations of tips and tubes or rods shown in FIGS. 3A-3J are contemplated.

Oral Product Properties

The oral product 110 can provide a favorable tactile experience (e.g., mouth feel). The oral product 110 can also retain its shape during processing, shipping, handling, and optionally use. As noted above, the oral product 110 includes a polymer matrix that does not appreciably dissolve or disintegrate when placed in an oral cavity and exposed to saliva. In some cases, the oral product 110 can have an elasticity allowing an adult tobacco consumer to work the product within the mouth. In some cases, the oral product 110 has at least some shape memory and thus can return to shape after being squeezed between teeth in an oral cavity. Working of the oral product 110 within the oral cavity can accelerate the release of the flavors, active ingredients, additives, and/or sweeteners within the polymer matrix. For example, nicotine and/or tobacco can be included in a polymer matrix including ethylene-vinyl acetate copolymer.

During use, the oral product 110 can absorb saliva into the polymer matrix. The saliva can cause celluloid fibers in the polymer matrix to swell, which can further increase access to different sections of the polymer matrix. Physical activity, such as chewing of the oral product in the mouth, can also accelerate the swelling of any celluloid fibers within the matrix and therefore the release of additives. Chewing can also break apart encapsulated ingredients and/or starch deposits within the matrix. As the oral product is chewed, saliva can access different sections of the polymer matrix. The oral product 110 can be chewed without significant and instantaneous permanent plastic deformation. As the product is chewed, it can become more pliable and additional additives can become available for release into the oral cavity. Some embodiments of the oral product 110 can be adapted to remain non-sticky during and after use. After prolonged use, certain embodiments of the oral product 110 will expand and become flatter. The oral product, however, can retain the essence of its original shape. The amount of deformation will depend on the duration of use and an amount of mouth force used. As the product is used, it can increase in both weight and volume, due to the swelling. With greater the physical manipulation, the oral product 110 will have a greater amount of swelling and thus have a larger weight gain. In certain embodiments, the oral product 110 will have an increase in weight of between 4 and 75 percent when chewed by an adult consumer for 30 minutes.

The particular materials used in the oral product 110 and the processing techniques discussed below can have an impact on the physical properties of the oral product. Moreover, the incorporation of air bubbles or channels, or different fillers and/or fibers can also have an impact on the elasticity and pliability of the oral product. Additionally, the material properties of the overall oral product 110 can change as tobacco constituents and/or other ingredients are released. In some cases, non-tobacco fibers and/or fillers can also dissolve or disintegrate during use and thus alter the material properties of the oral product 110 during use.

The oral product 110 can have a variety of colors. In some cases, natural and artificial coloring can be added to the mouth-stable polymer before or during the molding process to form oral products 110 having a predetermined color. Encapsulated flavors can be added during the extrusion process to create speckles, patterns or dots within the oral product.

Tobacco

In some cases, the oral product can include tobacco within the polymer matrix. Tobacco can be mixed with the polymer prior to or during an extrusion process. Tobacco fibers can provide passages in the polymer matrix, which can permit certain tobacco constituents and/or additives within the mouth-stable polymer matrix to be released into an oral cavity when the oral product is received in an oral cavity and exposed to saliva.

By "tobacco" it is meant a part, e.g., leaves, and stems, of a member of the genus *Nicotiana* that cut, shredded, or otherwise processed to form fibers of tobacco plant tissue. Exemplary species of tobacco include *N. rustica, N. tabacum, N. tomentosiformis*, and *N. sylvestris*. For example, the tobacco fibers can be obtained by comminuting tobacco stems. The tobacco can include cellulose, lignin, lipids, hemicellulose, and other tobacco constitutents.

Suitable tobaccos include fermented and unfermented tobaccos. In addition to fermentation, the tobacco can be processed using other techniques. For example, tobacco can be processed by heat treatment (e.g., cooking, toasting), flavoring, enzyme treatment, expansion and/or curing. Both fermented and non-fermented tobaccos can be processed using these techniques. In other embodiments, the tobacco can be unprocessed tobacco. Specific examples of suitable processed tobaccos include dark air-cured, dark fire-cured, burley, flue cured, and cigar filler or wrapper, as well as the products from the whole leaf stemming operation. In some cases, the tobacco fibers includes up to 70% dark tobacco on a fresh weight basis.

Tobacco can be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with the copolymer and optionally flavorants and other additives.

The tobacco can, in some cases, be prepared from plants having less than 20 μg of DVT per cm 2 of green leaf tissue. For example, the tobacco fibers can be selected from the tobaccos described in U.S. Patent Publication No. 2008/0209586, which is hereby incorporated by reference. Tobacco compositions containing tobacco from such low-DVT varieties exhibits improved flavor characteristics in sensory panel evaluations when compared to tobacco or tobacco compositions that do not have reduced levels of DVTs.

Green leaf tobacco can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (i.e., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660, 577; and 4,987,907.

The tobacco can be processed to a desired size. In certain cases, the tobacco fiber can be processed to have an average fiber size of less than 200 micrometers. In some cases, the tobacco fibers are between 75 and 125 micrometers. In other embodiments, the fibers are processed to have a size of 75 micrometers or less. In some cases, the tobacco fibers includes long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

The tobacco can have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. The oral product can have a different overall oven volatiles content than the oven volatiles content of the tobacco fibers used to make the oral product. The processing steps described herein can reduce or increase the oven volatiles content.

Additives

A variety of additives can be included in the oral product 110. The additives can include alkaloids (e.g., nicotine), minerals, vitamins, dietary supplements, nutraceuticals, energizing agents, soothing agents, coloring agents, amino acids, chemesthesis agent, antioxidants, food grade emulsifiers, pH modifiers, botanicals (e.g., green tea), teeth whitening (e.g., SHRIMP), therapeutic agents, sweeteners, flavorants, and combinations thereof. In certain embodiments, the additives include nicotine, sweeteners, and/or flavorants.

Nicotine

Nicotine added to the oral product can be tobacco-derived nicotine, synthetic nicotine, or a combination thereof. In certain embodiments, the oral product includes between 0.1 mg and 6.0 mg of nicotine. In some of these embodiments, the oral product includes between 1.0 mg and 3.0 mg of nicotine. As discussed above, nicotine can bind with the vinyl acetate in ethylene-vinyl acetate copolymer to slow the release of nicotine from an oral product.

Tobacco-derived nicotine includes one or more other tobacco organoleptic components other than nicotine. The tobacco-derived nicotine can be extracted from raw (e.g., green leaf) tobacco and/or processed tobacco. Processed tobaccos can include fermented and unfermented tobaccos, dark air-cured, dark fire-cured, burley, flue cured, and cigar filler or wrapper, as well as the products from the whole leaf stemming operation. The tobacco can also be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. By processing the tobacco prior to extracting nicotine and other organoleptic components, the tobacco-derived nicotine may include ingredients that provide a favorable experience.

The tobacco-derived nicotine can be obtained by mixing cured and fermented tobacco with water or another solvent (e.g., ethanol) followed by removing the insoluble tobacco material. The tobacco extract may be further concentrated or purified. In some cases, select tobacco constituents can be removed. Nicotine can also be extracted from tobacco in the methods described in the following patents: U.S. Pat. Nos. 2,162,738; 3,139,436; 3,396,735; 4,153,063; 4,448,208; and 5,487,792.

The nicotine can also be purchased from commercial sources, whether tobacco-derived or synthetic. In other embodiments, the oral product can include a derivative of nicotine (e.g., a salt of nicotine).

Sweeteners

A variety of synthetic and/or natural sweeteners can be used as additives in the oral product 110. Suitable natural sweeteners include sugars, for example, monosaccharides, disaccharides, and/or polysaccharide sugars, and/or mixtures of two or more sugars. According to some embodiments, the oral product 110 includes one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. The oral product 110 can also include non-nutritive sweeteners. Suitable non-nutritive sweeteners include: stevia, saccharin; Aspartame; sucralose; or acesulfame potassium.

Flavorants

The oral product 110 can optionally include one or more flavorants. The flavorants can be natural or artificial. For example, suitable flavorants include wintergreen, cherry and berry type flavorants, various liqueurs and liquors (such as Drambuie, bourbon, scotch, and whiskey) spearmint, peppermint, lavender, cinnamon, cardamon, apium graveolens, clove, cascarilla, nutmeg, sandalwood, bergamot, geranium, honey essence, rose oil, vanilla, lemon oil, orange oil, Japanese mint, cassia, caraway, cognac, jasmine, chamomile, menthol, ylang-ylang, sage, fennel, piment, ginger, anise, coriander, coffee, licorice, and mint oils from a species of the genus Mentha, and encapsulated flavors. Mint oils useful in particular embodiments of the oral product 110 include spearmint and peppermint. Synthetic flavorants can also be used. The particular combination of flavorants can be selected from the flavorants that are generally recognized as safe ("GRAS") in a particular country, such as the United States. Flavorants can also be included in the oral product as encapsulated flavorants.

In some cases, the flavorants in the oral product 110 are limited to less than 20 weight percent in sum. In some cases, the flavorants in the oral product 110 are limited to be less than 10 weight percent in sum. For example, certain flavorants can be included in the oral product 110 in amounts of about 1 weight percent to 5 weight percent.

Other Additives

The oral product 110 may optionally include other additives. For example, these additives can include non-nicotine alkaloids, vitamins, dietary minerals, other dietary supplements, and/or therapeutic agents. For example, suitable vitamins include vitamins A, B1, B2, B6, C, D2, D3, E, F, K, and P. For example, an oral product 110 can include C-vitamins. Suitable dietary minerals include calcium (as carbonate, citrate, etc.) or magnesium (as oxide, etc.), chromium (usually as picolinate), and iron (as bis-glycinate). One or more dietary minerals could be included in an oral product with or without the use of other additives. Other dietary supplements and/or therapeutic agents can also be included as additives.

The oral product 110 can also include fillers such as starch, di-calcium phosphate, lactose, sorbitol, mannitol, and microcrystalline cellulose, calcium carbonate, dicalcium phosphate, calcium sulfate, clays, silica, glass particles, sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), stabilizers (e.g., ascorbic acid and monosterol citrate, BHT, or BHA), disintegrating agents (e.g., starch, sodium starch glycolate, cross caramellose, cross linked PVP), pH stabilizers, or preservatives. In some cases, the amount of filler in the oral product 110 is limited to less than 10 weight percent in sum. In some cases, the amount of filler in the oral product 110 is limited to be less than 5 weight percent in sum. In some cases, the fillers are mouth stable. In some cases, the fillers can dissolve or disintegrate during use and thus result in an oral product that becomes more pliable during use. In some cases, the filler can be crisped rice and/or encapsulated ingredients, which can break when the oral product is chewed.

Non-Tobacco Fibers

The oral product can further include non-tobacco fibers within the polymer matrix. In some cases, the non-tobacco fibers are hydrophilic such that water-soluble additives can be wicked by the fibers. In some cases, the fibers can dissolve to leave channels.

The non-tobacco fibers can be non-tobacco celluloid fibers. The non-tobacco celluloid fibers can be derived from plant tissue. In some cases, the non-tobacco celluloid fibers includes cellulose. The non-tobacco celluloid fibers can further include lignin and/or lipids. Suitable sources for non-tobacco celluloid fibers include wood pulp, cotton, sugar beets, bran, citrus pulp fiber, switch grass and other grasses, Salix (willow), tea, and Populus (poplar). In some cases, the non-tobacco celluloid fibers can be plant tissue comprising various natural flavors, sweeteners, or active ingredients. In some cases, the oral product 110 can include nicotine as an additive (optionally with additional sweeteners and flavors) and a combination of both non-tobacco cellulosic fiber and tobacco fiber. In some alternative embodiments, additional cellulosic fiber can be derived from tobacco plant tissue (e.g., exhausted tobacco fibers).

The oral product 110 can also include soluble fibers. The soluble fibers can be adapted to dissolve when exposed to saliva when the oral product 110 is received in an oral cavity. Soluble fibers can be used with tobacco fibers to provide channels for additives to be released from the oral product. As the soluble fibers dissolve, the oral product 110 can become more flexible and the additional channels can open up to permit the release of additional tobacco constituents and/or additives. Suitable soluble fibers include psyllium fibers.

Plasticizers

The oral product 110 can also include one or more plasticizers. Plasticizers can soften the final oral product and thus increase its flexibility. Plasticizers work by embedding themselves between the chains of polymers, spacing them apart (increasing the "free volume"), and thus significantly lowering the glass transition temperature for the plastic and making it softer. Suitable plasticizers include propylene glycol, glycerin, vegetable oil, and medium chain triglycerides. In some cases, the plasticizer can include phthalates. Esters of polycarboxylic acids with linear or branched aliphatic alcohols of moderate chain length can also be used as plasticizers. Moreover, plasticizers can facilitate the extrusion processes described below. In some cases, the oral product 110 can include up to 20 weight percent plasticizer. In some cases, the oral product 110 includes between 0.5 and 10 weight percent plasticizer, the oral product 110 can include between 1 and 8 weight percent plasticizer, or between 2 and 4 weight percent plasticizer. For example, an oral product can include about 3 to 6.5 weight percent of propylene glycol.

Molding Processes

The oral product 110 can be produced by extruding a mouth-stable polymer with tobacco fibers to form a rod of a mouth-stable polymer matrix including tobacco fibers. The rod is cut into individual oral products. For example, ethylene-vinyl acetate copolymer can be introduced into an extruder along with tobacco fibers. A mixture of optional additives can also be introduced into the extruder. For example, the additives can include a surfactant and a sweetener (e.g., sucralose). The mixture of additives can be provided in slurry form or a dry mix of powdered additives. A first section of the extruder can melt and mix the ethylene-vinyl acetate copolymer at a temperature of about 100° C. The tobacco, surfactant and sweetener can then be added while the ethylene-vinyl acetate copolymer is maintained in a melted state. The mixture can then be extruded out of an extrusion die at a temperature of about 100° C.

The polymer matrix/tobacco composite can exit an extrusion die as a rod onto a moving conveyor. The extruded polymer-tobacco rod can then cut in a cutting process. The cutting can be hot-face cutting. Hot-face cutting can occur immediately after the rod exits the extrusion die. The cutting process can also include a process of rounding the edges of the cut polymer-tobacco composite. For example, a pelletizer can be used to round the edges. The pelletizer can also help to cool the oral products 110. In some cases, the extruded polymer-tobacco rod can be cooled prior to cutting. Before or after cutting, additional additives and/or flavorants can be added to the extruded polymer-tobacco composite.

In addition to the methods described above, there are many methods for making and shaping the oral products. In some cases, extruded and cut pieces can be introduced into a compression mold to form a final oral product shape. In some cases, the oral products 110 can be injection molded, compression molded, or injection-compression molded. Blocks of polymer and tobacco (and optionally other additives) can also be formed and machined into a desired shape.

OTHER EMBODIMENTS

It is to be understood that, while the invention has been described herein in conjunction with a number of different aspects, the foregoing description of the various aspects is intended to illustrate and not limit the scope of the invention, which is defined by the scope of the appended claims. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An oral product comprising:
  a polymer matrix including a copolymer of ethylene and a vinyl monomer, zein, gelatin, or any combination thereof;
  an alkaloid;
  a triglyceride including,
    medium chain triglycerides; and
  a cellulosic material including,
    microcrystalline cellulose.
2. The oral product of claim 1, further comprising:
  a vitamin.
3. The oral product of claim 1, further comprising:
  a dietary supplement.
4. The oral product of claim 1, further comprising:
  an amino acid.
5. The oral product of claim 1, further comprising:
  a mineral.
6. The oral product of claim 1, wherein the triglyceride is present in an amount less than or equal to 20 weight percent.
7. The oral product of claim 1, wherein the triglyceride is present in an amount ranging from 0.5 weight percent to 10 weight percent.
8. The oral product of claim 1, further comprising:
  a flavorant.
9. The oral product of claim 8, wherein the flavorant is an encapsulated flavorant.
10. The oral product of claim 1, further comprising:
  a sweetener.

11. The oral product of claim 10, wherein the sweetener includes saccharine, sucralose, aspartame, acesulfame potassium, or any combination thereof.

12. The oral product of claim 1, wherein the polymer matrix includes the copolymer of ethylene and the vinyl monomer.

13. The oral product of claim 12, wherein the copolymer of ethylene and the vinyl monomer includes vinyl acetate in an amount ranging from 25 weight percent to 40 weight percent.

14. The oral product of claim 12, wherein the copolymer of ethylene and the vinyl monomer is amorphous.

15. An oral product comprising:
- a polymer matrix including a copolymer of ethylene and a vinyl monomer, zein, gelatin, or any combination thereof;
- an energizing agent;
- a triglyceride including,
  - medium chain triglycerides; and
- a cellulosic material including,
  - microcrystalline cellulose.

16. The oral product of claim 15, further comprising:
- an additive including a mineral, a vitamin, a dietary supplement, a nutraceutical, a soothing agent, a coloring agent, an amino acid, a chemesthesis agent, an antioxidant, a food-grade emulsifier, a pH modifier, a botanical, a teeth whitening agent, a therapeutic agent, or any combination thereof.

17. The oral product of claim 15, wherein the triglyceride is present in an amount less than or equal to 20 weight percent.

18. The oral product of claim 15, further comprising:
- a flavorant, and
- a sweetener.

19. The oral product of claim 15, wherein the polymer matrix includes the copolymer of ethylene and a vinyl monomer.

20. The oral product of claim 19, wherein
- the copolymer of ethylene and the vinyl monomer includes vinyl acetate in an amount ranging from 25 weight percent to 40 weight percent, and
- the polymer matrix includes the copolymer of ethylene and a vinyl monomer.

* * * * *